US006551291B1

(12) United States Patent
de Juan, Jr. et al.

(10) Patent No.: US 6,551,291 B1
(45) Date of Patent: Apr. 22, 2003

(54) NON-TRAUMATIC INFUSION CANNULA AND TREATMENT METHODS USING SAME

(75) Inventors: Eugene de Juan, Jr., Phoenix, MD (US); Patrick S. Jensen, Cockeysville, MD (US); Terry H. Shelley, Hampstead, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/366,914

(22) Filed: Aug. 4, 1999

(51) Int. Cl.7 .............................................. A61M 35/00
(52) U.S. Cl. ...................................... 604/294; 604/289
(58) Field of Search ............................ 604/22, 27, 289, 604/290, 292, 293, 294, 296, 298, 297

(56) References Cited

U.S. PATENT DOCUMENTS

| 4,530,359 A | * | 7/1985 | Helfgott et al. ............. 128/329 |
| 4,692,142 A | | 9/1987 | Dignam et al. ................ 604/51 |
| D297,046 S | | 8/1988 | Dignam ........................ D24/8 |
| 4,781,675 A | | 11/1988 | White ........................... 604/10 |
| 5,032,111 A | * | 7/1991 | Morris et al. .................. 604/23 |
| 5,258,412 A | * | 11/1993 | Peyman et al. ............. 514/772 |
| 5,487,725 A | * | 1/1996 | Peyman ........................ 604/22 |
| 5,547,473 A | * | 8/1996 | Peyman ........................ 604/27 |
| 5,630,809 A | | 5/1997 | Connor ......................... 606/17 |
| 5,997,498 A | * | 12/1999 | De Juan, Jr. ................. 604/26 |

FOREIGN PATENT DOCUMENTS

| EP | 922466 | 6/1999 |
| WO | WO 98/35716 | 8/1998 |

\* cited by examiner

Primary Examiner—Manuel Mendez
(74) Attorney, Agent, or Firm—Peter F. Corless; Steven M. Jensen; Edwards & Angell, LLP

(57) ABSTRACT

In preferred aspects, the present invention features a non-traumatic cannula for use in connection with eye surgery, such as retinal tear and/or detachment surgery. The non-traumatic cannula of the present invention is particularly configured so as to minimize or avoid the potential for damage to the retina when infusing air or a gas therein. Related methods are also disclosed for infusing air during eye surgical procedures e.g. for treating a retinal tear or detachment and macular hole surgery. The method for infusing a fluid, such as a gas, into a patient's eye during eye surgery includes flowing the fluid from a fluid source to the patient's eye and diffusing the flowing fluid as it enters into the patient eye. Such a method further includes providing a non-traumatic cannula that is fluidly coupled to the fluid source, and which diffuses fluid exiting an end thereof. Thus, the fluid flowing out of the cannula is thereby diffusively infused.

19 Claims, 4 Drawing Sheets

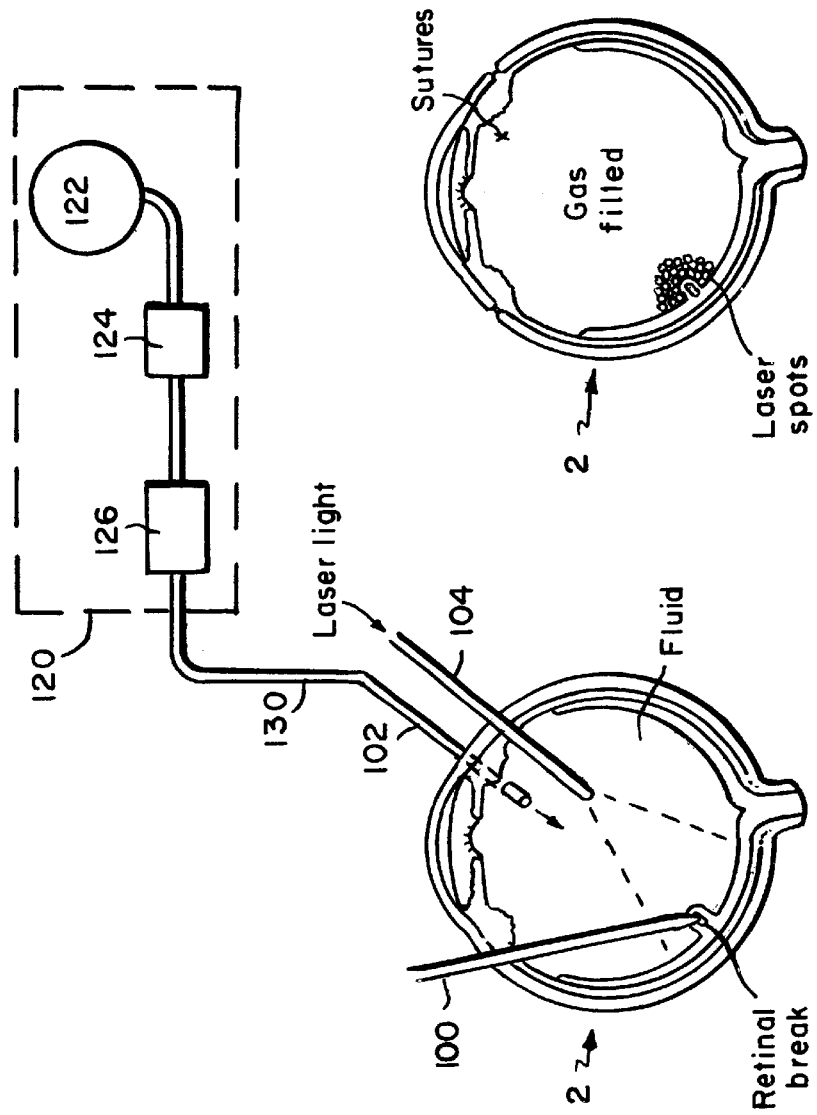
FIG. 7C
FIG. 7B
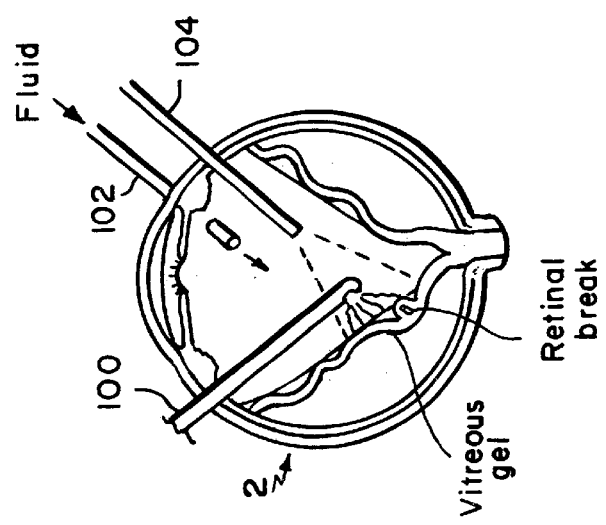
FIG. 7A

NON-TRAUMATIC INFUSION CANNULA AND TREATMENT METHODS USING SAME

BACKGROUND OF THE INVENTION

1. Field of the Invention

The present invention relates to cannulas used in connection with medical procedures and techniques, more particularly to cannulas used in procedures and techniques involving the eye and eye surgery (e.g., retinal tear or detachment surgery, macular hole surgery), as well as methods related thereto.

2. Background

Retinal tears can occur when the vitreous, a clear gel-like substance that fills the center of the eye, pulls away from the retina thereby leaving behind a tear or hole in the retina. Rhegmatogenous retinal detachments can result if the retinal breaks (i.e., tears or holes in the retina) are not treated. With retinal breaks, fluid from the vitreous apparently seeps through the retinal break and accumulates under the retina. The degree of detachment is measured by the volume of subretinal fluid present as well as the area of the retina involved. Some symptoms of retinal detachment include the presence of floaters, flashes, shadows or blind areas, decreased visual acuity and metamorphopsia.

A number of techniques may be employed for treating retinal detachments, including using a scleral buckle, pneumatic retinopexy, cryopexy (i.e., freezing) and photocoagulation using a laser or xenon arc light source. These techniques may be used alone or in combination with each other to treat the retinal detachments. For example, a combination of a scleral buckle and photocoagulation may be used in some cases. Alternatively, retinal tears with little or no nearby detachment may be treated using photocoagulation or cryopexy.

Using a laser in the photocoagulation technique, the retinal break is surrounded with one or more rows of a plurality of laser burns or laser heat spots. These laser burns or heat spots produce scars which prevent fluid from passing through and collecting under the retina. In the photocoagulation procedure, a gas is exchanged with the vitreous fluid being aspirated from within the eye so that the gas is intraocular when performing photocoagulation.

During vitreoretinal surgery, intraocular pressure is maintained by infusing a fluid, such as a buffered saline solution, from an elevated IV bottle into the eye through a cannula. Often the surgical procedures will call for air to be infused through the cannula while the fluid is being drained and/or aspirated through a second port or means. Recent findings discuss the potential for damage to the retina occurring during the fluid-air exchange.

Thus, it would be desirable to have improved devices, systems and methods for infusing a gas, particularly air, to a patient's eye during eye surgery procedures. It would be particularly desirable to have improved devices, systems and methods for infusing air or other gas to a patient's eye during surgery so as to limit or avoid the potential for damage to the retina as compared to prior art devices, systems, methods or techniques.

SUMMARY OF THE INVENTION

There has now been produced new devices and methods that enable infusing air or other gases to be infused into a patient's eye during surgical procedures (e.g. macular hole surgery) that minimize or avoid damage to the retina during the fluid-air exchange process, particularly when infusing a gas into the eye.

More particularly, the present invention features a non-traumatic cannula for use in connection with eye surgery, such as retinal tear and/or detachment surgery. The non-traumatic cannula of the present invention is particularly configured so as to minimize or avoid the potential for damage to the retina when infusing air or a gas therein. The invention also features related methods for infusing air during eye surgical procedures as well as methods for treating a retinal tear or detachment.

The methods of the invention generally comprise diffusively flowing a fluid into the ocular cavity of a patient's eye, typically during an eye surgery procedure. More particularly, the methods include providing a non-traumatic cannula having a lumen for transporting the fluid to be infused. One end of this non-traumatic cannula, which is in fluid communication with the lumen, includes a means for diffusing or disrupting the flow of fluid from the non-traumatic cannula so there is an infusion of fluid into the eye, which infusion is non-traumatic with respect to the retina. Typically, the fluid is in the form of a gas, although for many applications a liquid may be diffusively applied to a patient eye.

Preferred non-traumatic cannulas of the present invention include a fluid exit portion that includes a tubular member having an interior passage fluidly coupled to a fluid source. One end of the tubular member further includes a means or mechanism for diffusively infusing the fluid therein from the end of the tubular member.

The mechanism by which the fluid is diffusively infused is adapted for mechanical deflecting or re-directing the flow of fluid, creating turbulent flow from the tubular member end or porous diffusion of the fluid through the tubular member end. In that way, the flow into the ocular cavity is diffusive. The mechanism for mechanical deflecting of the fluid flow includes one of a baffle member, providing a cannula having a sealed end with opposed elongated slots in a side of the tubular member and a tubular member end having a multiple slotted end with a deflecting member disposed in the end.

The term "diffusive flow" of fluid or other similar terms to describe fluid exiting a device of the invention typically indicates the fluid is flowing in a turbulent, non-laminar manner. See *McGraw-Hill Encyclopedia of Science and Technology* (McGraw-Hill), incorporated herein by reference, for discussions of the terms turbulent and laminar. Preferably, fluid diffusively flowing out of a device of the invention onto a patient eye will have a Reynolds number ($pvd/\mu$) of greater than about 2,000, more typically greater than 2,400 or 2,500, more preferably a Reynolds number of greater than 2,800, 2,900 or 3,000.

Other aspects and embodiments of the invention are discussed infra.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein:

FIGS. 7A–C are cross-sectional schematic views of an eye undergoing a retinal tear repair procedure while using a non-traumatic cannula of the present invention.

DETAILED DESCRIPTION OF THE INVENTION

Figure 1A:
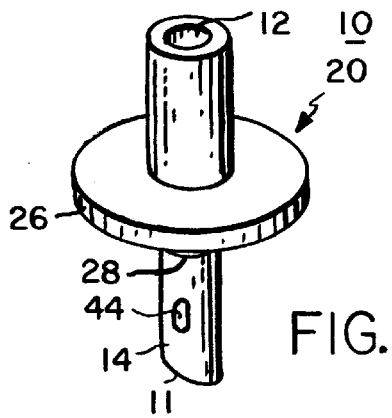
FIG. 1A is a perspective view of a non-traumatic cannula according to the present invention.

Referring now to the various figures of the drawing wherein like reference characters refer to like parts, there is shown in FIGS. 1A,B a non-traumatic cannula 10 according to the present invention for use in surgical procedures such as vitreoretinal surgical procedures. The non-traumatic cannula 10 includes a lumen 12 that extends along the length of the non-traumatic cannula, an exit end portion 14 that enters the ocular cavity, a connecting member 20 having a supply end 22 or rearward end that is connected to an external fluid or fluid pressure source 120 (FIG. 7B), generally by means of external tubing 130. The exit end portion 14 and the connecting member 16 are fluidly coupled to the lumen 12 and thus fluidly coupled to each other so the external fluid is communicated via the lumen to the exit end portion.

The exit end portion 14 of the non-traumatic cannula 10 is configured or arranged so that the fluid exiting the end portion diffusively flows outwardly from the exit end portion. In this way, the fluid exiting the non-traumatic cannula 10 does not form a fluid stream or fluid jet that is projected directly at a single opposing surface. Such a configuration avoids or minimizes the potential for mechanical damage to the opposing surface. Additionally, when the fluid is a gas, the diffusiveness of the fluid exiting the exit end portion 14 also decreases the potential for damage to retinal tissue resulting from dehydration.

There are described herein, in connection with FIGS. 2–6, a number of illustrative embodiments for such an exit end portion 14 by which the fluid exits the non-traumatic cannula 10 diffusively. One of those illustrative embodiments uses elongated ports 44 (FIGS. 1A and 3A,B). For details of the construction and arrangement of this particular embodiment, specific reference shall be made to the following discussion regarding FIGS. 3A,B.

Figure 1B:
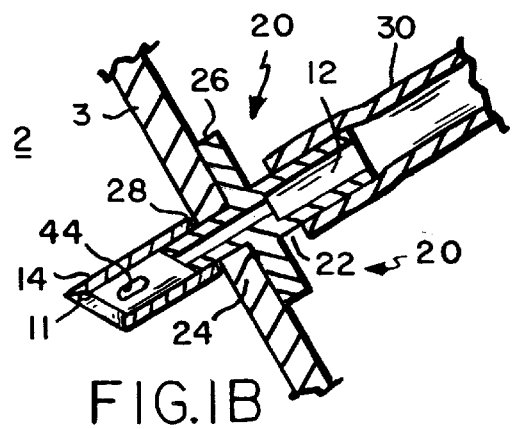
FIG. 1B is a cross-sectional view of the non-traumatic cannula of FIG. 1A when inserted into an eyeball.
Figure 2A:
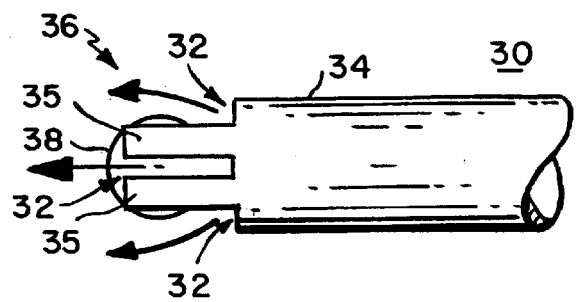
FIG. 2A is a side view of an end portion according to a first embodiment of the present invention for the non-traumatic cannula of FIG. 1.
Figure 2B:
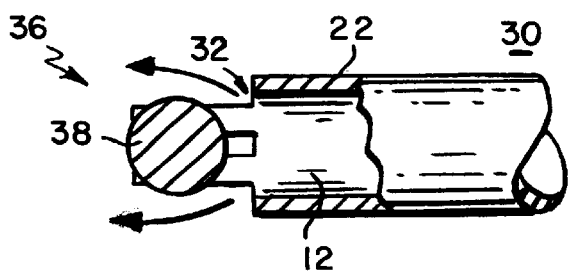
FIG. 2B is the side view of the non-traumatic cannula end portion of FIG. 2A further including a partial cross-sectional cutaway view.

In the illustrated embodiments, the supply end 22 is sized so as to be snugly inserted inside the flexible fluid delivery tubing 130 in a fluid-tight manner (see FIGS. 1B and 2B). It is within the scope of the present invention, however, for such tubing to be secured to the supply end 22 using any of a number of means known to those skilled in the art including clamping devices, threaded connections, and Luer-Lock type of connections. In sum, any conventional manner capable of withholding fluid under pressure may be utilized.

Referring to FIGS. 1A,B, in addition to the supply end 22, the interconnecting member 20 includes a neck portion 24 and a flange 26. The neck portion 24 is of lesser diameter than the exit end portion 14. As such, when the exit end portion 14 and the neck portion 24 are interconnected to each other so as to establish a fluid tight connection therebetween, the two portions form a shoulder 28 at the point of transition. In preferred embodiments, such as that shown, the forward and neck portions are coaxial, and the shoulder is a flat circumferential surface generally perpendicular to the axis of the non-traumatic cannula and encircling the cannula.

The width of the shoulder 28 may vary, but is generally selected such that it is sufficient to retain the sclera 3 of the eye 2 as the hole in the sclera contracts around the neck portion 24 due to the resiliency of the sclera once it has passed over the shoulder 28. In an exemplary embodiment, the difference in diameter between the neck and forward portions of the cannula is conveniently achieved by fusing together two hypodermic needles of appropriate diameter. As an example, the diameter of the neck portion 24 may be 20-gauge with a 19-gauge for the exit end portion 14.

The flange 26 is spaced from the shoulder 28 a sufficient distance to retain the thickness of the sclera, and preferably is slightly larger than a typical sclera thickness. The width of the flange 26 also can be considerably greater than the width of the shoulder 28 because the flange is retained outside the eye 2 so as to function as a stop limiting the degree of insertion of the cannula.

The piercing end 11 of the cannula exit end portion 14 is a solid member that seals the circular opening forming one end of the lumen 12. In this way, fluid flow in the lumen 12 is directed within the exit end portion so that it flows out of each elongated port 44 or other means provided for diffusively infusing the fluid into the ocular cavity. In the illustrated embodiment, the piercing end also is cut at an acute angle with respect to the cannula axis to facilitate piercing of the sclera 3.

Typically, to insert such a non-traumatic cannula 10 into the eye for surgical purposes, one pierces the external surface of the sclera 3 with the piercing end 11, and advances the cannula forward into the interior of the eye 2 until the shoulder 28 passes the internal surface of the sclera. The sclera 3 then rests between the shoulder 28 and the flange 26 and closes around the neck portion 24 due to its own resiliency. Preferably, the flange 26 rests against the external surface of the sclera.

Once insertion is completed, fluid is delivered through the fluid delivery tubing 130 and out of the elongated ports 44 into the ocular cavity or interior of the eye 2. The surgical operation then proceeds, generally involving instruments piercing the eyeball at other points. Once the operation is completed, the non-traumatic cannula 10 is removed by pulling outward while applying gentle pressure on the sclera external surface immediately adjacent to the cannula.

The foregoing discussion is illustrative of how one readily available cannula can be adapted in accordance with the teachings of the present invention so as to yield a non-traumatic cannula 10 of the present invention. As such, the foregoing discussion and the following discussion of the various specific embodiments shall not be limited to only the specific type of cannula described in connection with FIGS. 1A,B. Rather, it is within the scope of the present invention to adapt any of the exit end portions or the means for diffusively infusing fluid into the ocular cavity as described herein for use in any commonly available cannula.

Figure 2C:
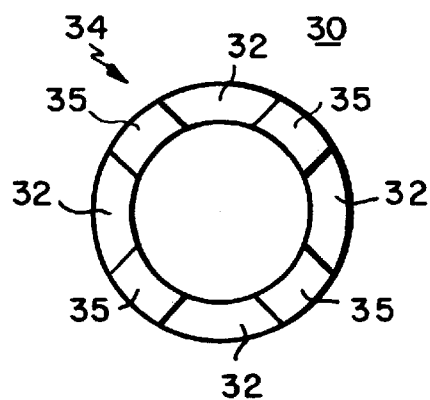
FIG. 2C is an end view of the non-traumatic cannula end portion of FIG. 2A.

There is shown in FIGS. 2A–C, a first embodiment of an exit end portion 30 according to the present invention for a non-traumatic cannula 10, that includes one or more slits 32 or openings extending lengthwise in a tubular member 34 and disposed circumferentially about a distal end 36 of the tubular member. In preferred embodiments, the slits 32 are equiangularly spaced from each other about the circumference and more preferably there are a multiplicity of equiangularly spaced slits.

These lengthwise extending slits 32, in effect, create a plurality or a multiplicity of finger like structures 35 that also extend lengthwise at the tubular member distal end 36. Although the slits 32 are shown as extending lengthwise to the end of the tubular member 34, this is not a limitation. Rather, the slits 32 can be stopped short of the end of the tubular member 34 so that a circumferential band is formed proximal to the tubular member end.

The exit end portion 30 also includes a deflecting member 38 that is disposed and secured within the generally circular exit aperture formed by the finger like structure 35 and/or circumferential band so as to generally occlude the exit aperture but not fully occlude the slits 32. In this way, the fluid flowing in the lumen 12 is re-directed by the deflecting member 24 so that the fluid flows outwardly through each of the slits 32.

In an exemplary embodiment, the deflecting member 38 is a spherical member, for example a ball bearing. This is not a limitation as the deflecting member 38 can have any geometric configuration that can be secured within the exit aperture as herein described. For example, when the tubular member 34 and the deflecting member 38 are metals, the deflecting member 24 is pressed into the exit aperture and then attached thereto by means of resistance welding. However, it is within the scope of the present invention for the deflecting member 38 to be secured to the finger like structures 35 of the tubular member 34 by any means known to those skilled in the art.

The number and size of the slits 32 are established so that the fluid flow is deflected into different directions while minimizing pressure losses to an acceptable level. In an exemplary embodiment, the end portion 30 is made from a 20 gauge hypodermic tube and is configured with at least two diametrically opposed-slits 32 and more particularly with four equiangularly disposed slits that are about 1 mm long and about 0.25 to 5 mm in diameter.

Additionally, although the slits 32 are illustrated as being rectilinear, it is within the scope of the present invention for the slits to have any geometric shape for such an application. For example, the slits 32 can be generally oval or triangular in shape. As illustrated in FIG. 2C the walls comprising each slot 32 can be sloping.

Figure 3A:
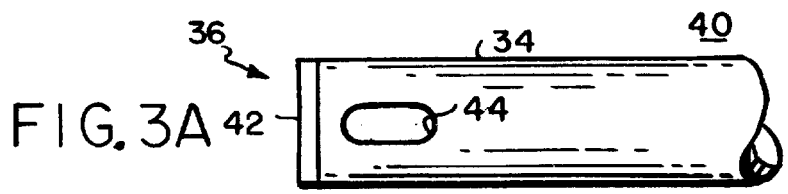
FIG. 3A is a side view of an end portion according to a second embodiment of the present invention for the non-traumatic cannula of FIG. 1.
Figure 3B:
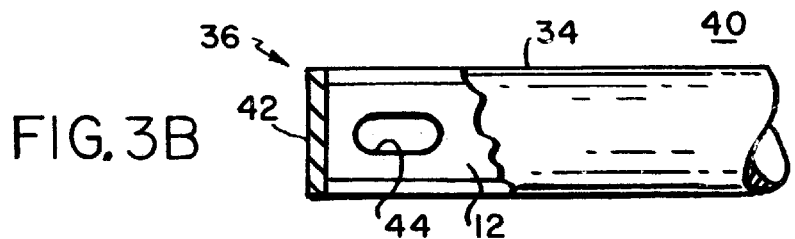
FIG. 3B is the side view of the non-traumatic cannula end portion of FIG. 3A further including a partial cross-sectional cutaway view.

Now referring to FIGS. 3A,B, there is shown a second embodiment of an exit end portion 40 according to non-traumatic cannula 10 of the present invention. The exit end portion includes a tubular member 34 and an end sealing member 42 at the distal end 36 thereof. The tubular member 34 also is configured with a plurality of elongated ports 44 that are diametrically opposed to each other and located proximal to the tubular member distal end 36. Alternatively, the tubular member 34 can be configured with a multiplicity of such elongated ports 44 that are equiangularly spaced from each other about the circumference of the tubular member. In an exemplary embodiment, the elongated ports are each about 2 mm in length and about 0.25 to 5mm in diameter.

The end sealing member 42 is sealingly secured to the distal end 36 of the tubular member 34 so as to occlude and seal the exit aperture formed therein by the lumen 12. In this way, the fluid that is flowing in the lumen 12 is re-directed so as to flow outwardly through each of the elongated ports 44 and thus dispersively into the ocular cavity.

In the illustrated embodiment, the end sealing member 42 is a flat, plate-like member that abuts the flat surfaces formed by the walls of the tubular member 34. This is not a limitation as the end sealing member 42 can have any geometric configuration that can be secured to the tubular member, for example a member having an arcuate surface and an opposing flat surface that is secured to the tubular member. Alternatively, the end sealing member 42 is a plug like member, a portion of which extends a distance into the lumen 12 but without occluding, or without significantly occluding, the elongated ports 44.

In an exemplary embodiment, the end sealing member 42 is secured to the tubular member 34 by suitable mean e.g. soldering or welding. However, it is within the scope of the present invention for the end sealing member 42 to be secured to the tubular member using any of a number of techniques known to those skilled in the art including, resistance welding, soldering, or other mechanical means such as threaded connections or adhesives as well as a combination thereof.

Figure 4A:
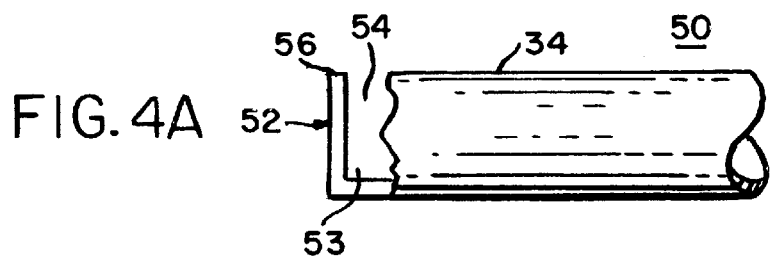
FIG. 4A is a side view of an end portion according to a third embodiment of the present invention for the non-traumatic cannula of FIG. 1.
Figure 4B:
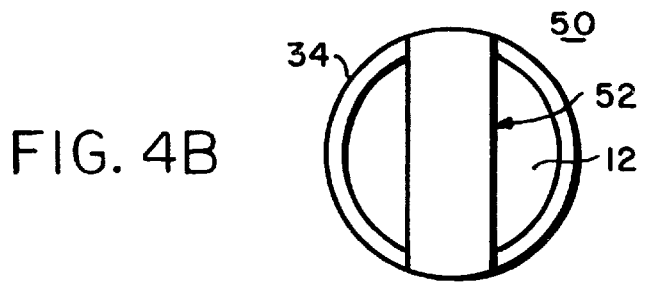
FIG. 4B is an end view of the non-traumatic cannula end portion of FIG. 4A.

Referring now to FIGS. 4A,B, there is shown an exit end portion 50 according to a third embodiment of the present invention for a non-traumatic cannula 10. Such an exit end portion 50 includes a tubular member 34 and a baffle member 52 being secured to the distal end 36 of the tubular member and spaced a distance from the exit aperture 54 formed by the lumen 12. The baffle member 52 also is sized and configured so it at least partially occludes the exit aperture 54. It also is within the scope of the present invention for the baffle member 52 to be arranged so that it occludes the exit aperture 54. In this way, the fluid exiting the exit aperture flows outwardly through the annular space 53 between the baffle member 52 and the tubular member 34.

The baffle member 52 splits the fluid flowing from the tubular member exit aperture 54, thereby generating turbulent fluid flow. The baffle member 52 also redirects the flow of the exiting fluid so that it does not directly impact an area within the ocular cavity directly opposite the exit aperture 54. In an exemplary embodiment, the baffle member 52 is formed by machining off a portion of 20 gauge hypodermic tubing. The remaining portion of the tubing is then bent such that it lies over the opening in the tubing and at least partially occludes the opening.

Although the cross portion 56 of the baffle member 52 is illustrated as having a generally rectilinear shape and being generally flat in cross section, this is not a limitation. It is within the scope of the present invention for the baffle member cross portion 56 to be formed in any geometric shape such as ovals or members having arcuate long sides extending across the exit aperture 54. The surface of the baffle member coming into contact with the external surface of the sclera can be flat as illustrated, a sloping surface as shown in FIG. 1B or have any geometric shape including arcuate surfaces (e.g., a portion of a spherical surface).

In an exemplary embodiment, the baffle member 52 and the tubular member 34 are formed so as to be an integral structure as described above. It is within the scope of the present invention, however, for the baffle member 52 to be secured to the tubular member using any of a number of techniques known to those skilled in the art. Such techniques include resistance welding, soldering, or other mechanical means such as threaded connections or adhesives as well as a combination thereof. Alternatively, the baffle member 52 can be am extended portion of a hollow plug member, where the hollow plug portion is inserted into the tubular member exit aperture 54 and secured therein.

Figure 5:
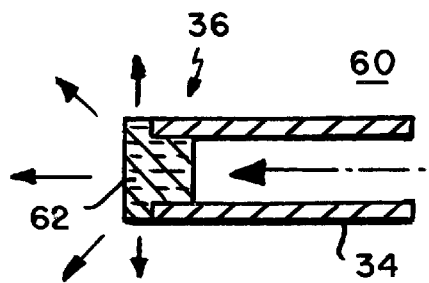
FIG. 5 is a cross section view of an end portion according to a fourth embodiment of the present invention for the non-traumatic cannula of FIG. 1.

Now referring to FIG. 5, there is shown an exit end portion 60 according to a fourth embodiment of the present invention for a non-traumatic cannula 10. Such an exit end portion 60 includes a tubular member 34 and a plug member 62 that is secured to the distal end 36 of the tubular member. The plug member 62 is made of a porous material, for example a sintered or foam-like material. In this way, the fluid contained within the lumen 12 flows diffusively through the porous or foam like material comprising the plug member 62, thence out through the exposed surfaces of the plug member 62, and thence dispersively into the ocular cavity.

Alternatively, the plug member 62 is made from an essentially solid material plug that is arranged to include a plurality, preferably a multiplicity, of through holes made or formed therein so that fluid in the lumen 12 flows through each of the through holes in the plug member, and thence dispersively into the ocular cavity.

Additionally, the plug member 62 can be configured so as to include therein an axial extending cavity that is fluidly coupled to the lumen 12 and so that the multiplicity of through holes extend from the axial extending cavity to the exposed surfaces of the plug member. In this way, fluid in the lumen 12 flows through the axial extending cavity, thence through the through holes, and thence dispersively into the ocular cavity. A variety of materials can be employed for the diffusive plug member, e.g. a sintered material that does not substantially inhibit air flow.

Figure 6:
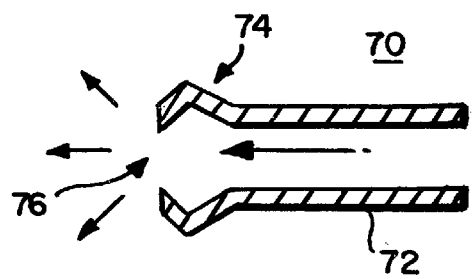
FIG. 6 is a cross-section view of an end portion according to a fifth embodiment of the present invention for the non-traumatic cannula of FIG. 1.

Now referring to FIG. 6, there is shown an exit end portion 70 according to a fifth embodiment of the present invention for a non-traumatic cannula 10. Such an exit end portion 70 includes a tubular member 72 having a nozzle 74 at the distal end of the tubular member and which is fluidly coupled to the lumen 12. In this way, fluid in the lumen 12 flows directly through the nozzle 74 and out the through aperture 76 therein and thus into the ocular cavity.

The nozzle 74 is arranged or configured such that the nozzle creates a level of turbulence in the fluid flow exiting the nozzle aperture 76 at the flow rates and pressures for typical applications. Such turbulent flow conditions result in the exiting fluid flow being dispersed at different angles with respect to the axis of the nozzle and thus, being diffusively infused into the ocular cavity.

The use of a non-traumatic cannula 10 of the present invention configured with any of the above described mechanisms or means for diffusing the flow of a fluid from an end thereof (see FIGS. 2–6), can be further understood from the following discussion relating to a method for treating a retinal tear or detachment by means of the laser photocoagulation technique and with reference to FIGS. 7A–C. Reference also shall be made to FIGS. 1–6 for specific components or elements of the non-traumatic cannula of the present invention not otherwise shown in FIGS. 7A–C.

In treating a retinal tear or detachment using a photocoagulation technique employing a laser, a cutting/aspirating instrument 100, a non-traumatic cannula 102 according to the present invention and a light transmitting instrument 104 are inserted through the sclera 3 so one end of each resides intraocular. The light transmitting instrument 104 is configured so the light from the laser (not shown) can be directed to specific locations on the retina. The cutting/ aspirating instrument is disposed so an end thereof is proximate the retinal tear.

Initially, the vitreous gel, especially all strands causing traction on the retinal tear are removed or aspirated by means of the cutting/aspirating instrument 100. As the vitreous gel is being aspirated, the intraocular volume is maintained by a continuous infusion of a fluid, such as a balanced salt solution (BSS), through the non-traumatic cannula 102. Any subretinal fluid also is aspirated through the retinal tear. Thereafter, the vitreous fluid is aspirated and exchanged with a gas such as air passing through the non-traumatic cannula 102.

In the method of the present invention, the gas or air being exchanged is provided by gas source that can comprise, for example, a gas supply and humdification system 120 that provides filtered, humidified air as shown in FIG. 7B and described in U.S. Ser. No. 09/074,960, the teachings of which are incorporated herein by reference. Such a system includes a gas supply 122, a filter 124 and an in-line humidifier 126 that humidifies the filtered gas. As described above, this gas supply and humidification system 120 is fluidly coupled to the non-traumatic cannula 102 by means of delivery tubing 130.

The retina surrounding the tear is then repeatedly exposed to the laser light from the light transmitting instrument 104 so as to form a plurality of heat spots on the retina surrounding the retinal tear. In particular, the practitioner manipulates the light transmitting instrument 104 so that a plurality of rows of a plurality of such heat spots surrounds the retinal tear. In this way, the retinal tear is photocoagulated with a laser to achieve a thermal adhesive injury. The heat spots also produce scars that prevent fluid from passing through and collecting under the retina.

Thereafter, the intraocular gas or air, infused while exposing the retina surrounding the retinal tear to laser light, is totally exchanged for a longer-lasting gas, such as sulfur hexafluorine or perfluoro propane. This gas allows an adequate tamponade time for the therapeutic chorioretinal scar to develop. Preferably, the longer lasting gas being infused is humidified using the in-line humidifier 126 and gas supply and humidification system 120. After completing the "in eye" portion of the treatment procedure, the inserted instruments and non-traumatic cannula are removed from the eye 2 and the spent components are disposed of in accordance with normal and usual practices. For purposes of easily maintaining sterility, it is preferred to replace the non-traumatic cannula 102 after surgery or following use.

The cannula and methods of the invention are also particularly useful in macular hole surgery procedures.

Figure 8:
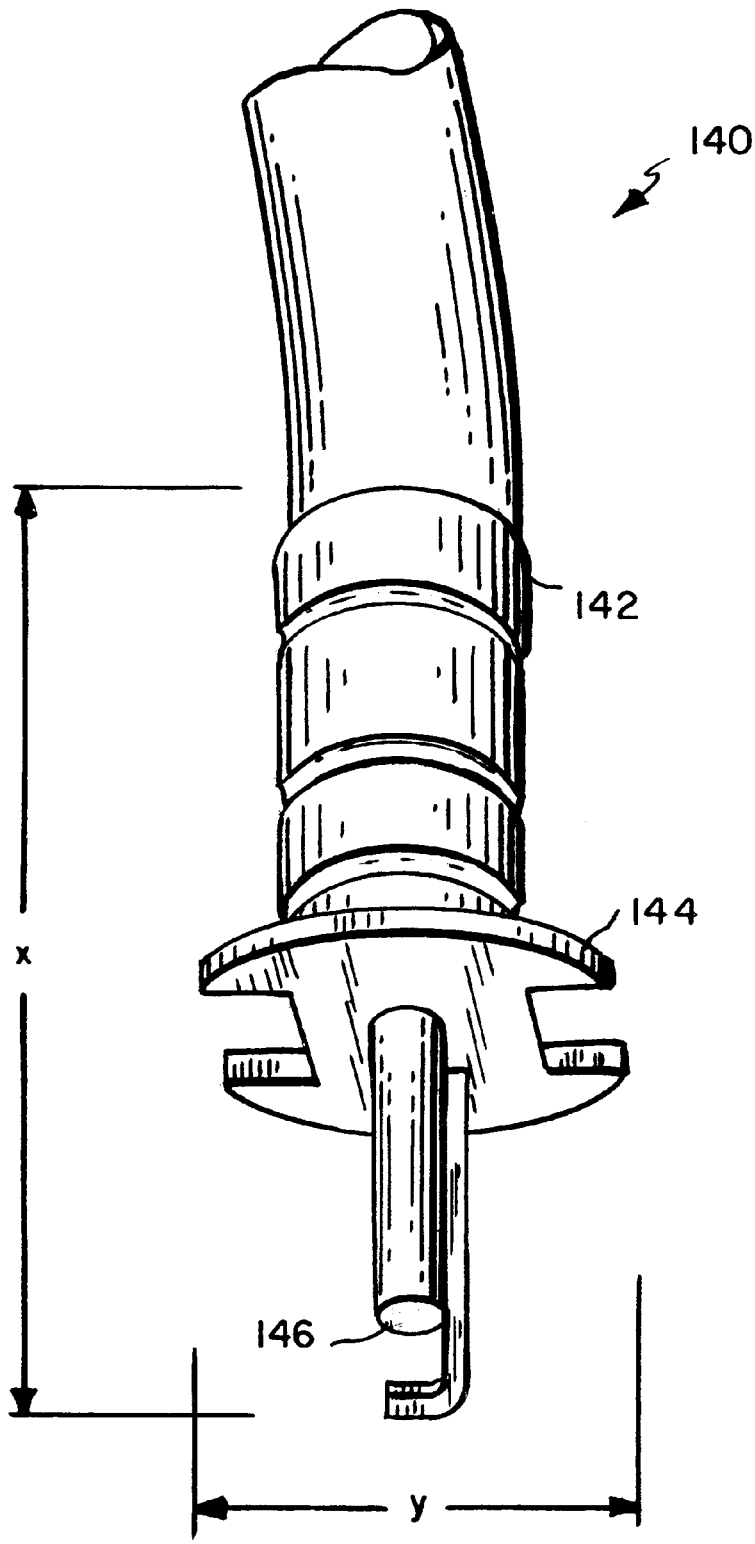
FIG. 8 depicts a further depiction of a preferred cannula of the invention.

FIG. 8 of the drawings depicts a further preferred cannula 140 of the invention that includes shaft 142 with distal diffusing and exit portion 144 from which a fluid (gas or liquid) diffusively exits via opening 146. Preferably, the depicted length x of portion 142 is 0.35 inches, and the width y of portion 144 is 0.19 inches. Preferably, portion 144 is formed from stainless steel.

The invention also includes device kits including a non-traumatic cannula 102 in an assembled configuration with or without interconnecting tubing packaged in a sterile condition. Alternatively, a non-traumatic cannula 102 can be supplied in the sterile packaging for later assembly by the practitioner. Preferably, it is provided in its assembled condition.

Although a preferred embodiment of the invention has been described using specific terms, such description is for illustrative purposes only, and it is to be understood that changes and variations may be made without departing from the spirit or scope of the following claims.

What is claimed is:

1. A method for treating a retinal tear of a patient eye, comprising:

maintaining the interocular volume of the patient eye by infusing a fluid therein; and diffusively infusing a first fluid into the patient eye while aspirating vitreous fluid therefrom, such that the first fluid flows in a turbulent, non-laminar manner.

2. The method for treating a retinal tear according to claim 1, further comprising:

providing a cannula having an exit end arranged so the fluid exiting therefrom is dispersed; and wherein said diffusively infusing includes:
      inserting the exit end of the cannula into the eye, and flowing the fluid out of the exit end into the patient eye.

3. The method for treating a retinal tear according to claim 2, wherein the cannula being provided includes:

a flow member having a lumen through which the fluid flows, where an end of the flow member comprises a plurality of circumferentially disposed, axial extending through apertures; and a deflecting member being secured in a lumen opening at the flow member end having the plurality of through apertures so as to substantially occlude the lumen opening but not fully occlude the plurality of through apertures, whereby the fluid flowing in the lumen exits through each through aperture.

4. The method for treating a rectinal tear according to claim 3, wherein the plurality of through apertures are equiangularly spaced about the circumference of the flow member.

5. The method for treating a retinal tear according to claim 3, wherein the flow member end with the through apertures is configured with a multiplicity of through apertures.

6. The method for treating a retinal tear according to claim 3, wherein the plurality of through apertures form finger-like structures and wherein the deflecting member is secured to the finger-like structures.

7. The method for treating a retinal tear according to claim 3, wherein the flow member is tubular and wherein the deflecting member is spherical.

8. The method for treating a retinal tear according to claim 2, wherein the cannula being provided includes:

a flow member having a lumen through which the fluid flows;

wherein a lumen opening at one end of the flow member is sealed; and wherein the flow member proximal to the sealed end comprises a plurality of equiangularly spaced, axial extending through apertures provided in the axial extending surface of the flow member, whereby the fluid flowing in the lumen exits through each through aperture.

9. The method for treating a retinal tear according to claim 8, wherein the flow member is configured with a multiplicity of through apertures proximal to the sealed end.

10. The method for treating a retinal tear according to claim 2, wherein the cannula being provided includes:

a flow member having a lumen through which the fluid flows;

a baffle member being secured to an end of the flow member having a lumen opening and being configured so as to partially occlude the lumen opening, whereby fluid exiting the lumen opening is re-directed by the baffle member.

11. The method for treating a retinal tear according to claim 10, wherein:

the baffle member is spaced a distance from the lumen opening; and the baffle member is substantially equal in size and shape to that of the lumen opening so that fluid exiting the lumen opening is redirected so as to flow out from an annular space formed between the baffle member and the end of the flow member having the lumen opening.

12. The method of claim 1 wherein the fluid is a liquid.

13. The method of claim 1 wherein the fluid is a gas.

14. The method of claim 1 wherein fluid infused to the patent eye has a Reynolds number of greater than about 2,000.

15. The method of claim 1 wherein fluid infused to the patent eye has a Reynolds number of greater than about 2,400.

16. The method of claim 1 wherein fluid infused to the patent eye has a Reynolds number of greater than about 2,800.

17. The method of claim 1 wherein fluid infused to the patent eye has a Reynolds number of greater than about 3,000.

18. The method for treating a retinal tear according to claim 1, further comprising:

photocoagulating an area of the retina surrounding the retinal tear; and exchanging the first infused fluid with a second fluid.

19. The method for treating a retinal tear according to claim 18, further comprising the step of humidifying the first fluid being infused.

* * * * *